(12) United States Patent
Gradon et al.

(10) Patent No.: US 6,615,834 B2
(45) Date of Patent: Sep. 9, 2003

(54) NASAL MASK

(75) Inventors: Lewis George Gradon, Auckland (NZ); Nicholas Charles Alan Smith, Auckland (NZ); Alastair Edwin McAuley, Auckland (NZ); Mark Joseph Haycock, Auckland (NZ); Chris Earl Nightingale, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

(21) Appl. No.: 09/881,633

(22) Filed: Jun. 14, 2001

(65) Prior Publication Data

US 2002/0005201 A1 Jan. 17, 2002

(30) Foreign Application Priority Data

| Jun. 14, 2000 | (NZ) | ............................................. 505154 |
| Jun. 14, 2000 | (NZ) | ............................................. 505155 |
| Jun. 14, 2000 | (NZ) | ............................................. 505156 |
| Nov. 16, 2000 | (NZ) | ............................................. 508218 |
| Nov. 16, 2000 | (NZ) | ............................................. 508219 |
| Nov. 27, 2000 | (NZ) | ............................................. 508433 |
| Dec. 20, 2000 | (NZ) | ............................................. 509039 |

(51) Int. Cl.$^7$ .............................................. A62B 18/08
(52) U.S. Cl. ................................................. 128/207.11
(58) Field of Search ....................... 128/204.13, 206.27, 128/207.11, 207.17, 206.12, 206.18, 206.21, 206.28, 207.13

(56) References Cited

U.S. PATENT DOCUMENTS 6,044,844 A * 4/2000 Kwok et al. ........... 128/207.11

* cited by examiner

Primary Examiner—William C. Doerrler
Assistant Examiner—Mailk N. Drake
(74) Attorney, Agent, or Firm—Trexler, Bushnell, Giangiorgi, Blackstone & Marr, Ltd.

(57) ABSTRACT

A improved nasal mask is disclosed for delivering CPAP therapy to patients. The nasal mask has a sliding engagement to the headgear. The sliding engagement allows substantial relative lateral movement eg: when face is distorted from sleeping on side, while still providing adequate compressive force to avoid side leakage. The sliding engagement also allows easy release from the headgear.

19 Claims, 6 Drawing Sheets

NASAL MASK

FIELD OF INVENTION

This invention relates to nasal masks particularly though not solely for use in providing CPAP therapy to patients suffering from obstructive sleep apnoea (OSA).

BACKGROUND OF THE INVENTION

In the art of respiration devices, there are well known a variety of respiratory masks which cover the nose and/or mouth of a human user in order to provide a continuous seal around the nasal and/or oral areas of the face such that gas may be provided at positive pressure within the mask for consumption by the user. The uses for such masks range from high altitude breathing (i.e., aviation applications) to mining and fire fighting applications, to various medical diagnostic and therapeutic applications.

One requisite of such respiratory masks has been that they provide an effective seal against the user's face to prevent leakage of the gas being supplied. Commonly, in prior mask configurations, a good mask-to-face seal has been attained in many instances only with considerable discomfort for the user. This problem is most crucial in those applications, especially medical applications, which require the user to wear such a mask continuously for hours or perhaps even days. In such situations, the user will not tolerate the mask for long durations and optimum therapeutic or diagnostic objectives thus will not be achieved, or will be achieved with great difficulty and considerable user discomfort.

In common with prior art designs, is an inability to seal effectively when the user's face becomes distorted. For example, as shown in the prior art mask of FIG. 1 when the user 300 is sleeping on his or her side, one side 302 of the headgear tends to be pulled tight while the other side 304 tends to be loose. This causes the axis of the mask 306 to be twisted with respect to the axis of the head 308—due to the net torque from the headgear—resulting in leakage 310 on one side. The user 300 sleeping on his or her side may also distort the facial contours around the nasal area 312 and may lead to further leakage.

SUMMARY OF INVENTION

It is an object of the present invention to provide a nasal mask which goes some way to overcoming the abovementioned disadvantages in the prior art or which will at least provide the industry with a useful choice.

Accordingly in one aspect the invention consists in a device for delivering a supply of gases to a user comprising:
 a patient interface, in use in fluid communication with said supply of gases,
 securement means attached to or around the head of said user, and
 engaging means adapted to slidingly engage said securement means with said patient interface.

In a second aspect the present invention consists in nasal mask for delivering gases to a user comprising:
 a body portion having a inlet, in use said inlet receiving a supply of gases,
 sealing means engaged with said body portion, and adapted to seal against the facial contours of said user, and
 engaging means adapted to in use provide a sliding engagement with a means of securement to a user, and a compressive force on said sealing means to ensure said supply of gases is delivered to a user without significant leakage.

In a third aspect the present invention consists in a CPAP system for delivering gases to a user including a pressurised source of gases, transport means in fluid communication with said pressurised source adapted to convey said gases, and a nasal mask in fluid communication with said transport means in use delivering said gases to said user, said nasal mask comprising
 a body portion having a inlet, in use said inlet receiving a supply of gases,
 sealing means engaged with said body portion, and adapted to seal against the facial contours of said user, and
 engaging means adapted to in use provide a sliding engagement with a means of securement to a user, and a compressive force on said sealing means to ensure said supply of gases is delivered to a user without significant leakage.

This invention may also be said broadly to consist in the parts, elements and features referred to or indicated in the specification of the application, individually or collectively, and any or all combinations of any two or more of said parts, elements or features, and where specific integers are mentioned herein which have known equivalents in the art to which this invention relates, such known equivalents are deemed to be incorporated herein as if individually set forth.

The invention consists in the foregoing and also envisages constructions of which the following gives examples.

BRIEF DESCRIPTION OF THE DRAWINGS

One preferred form of the present invention will now be described with reference to the accompanying drawings in which.

DETAILED DESCRIPTION OF THE PREFERRED EMBODIMENTS

The present invention provides improvements in the field of nasal masks for use in CPAP therapy. In particular a nasal mask is described which is more comfortable for the user to wear and reduces the side leakage as compared with masks of the prior art. It will be appreciated that the nasal mask as described in the preferred embodiment of the present invention can be used in respiratory care generally or with a ventilator but will now be described below with reference to use in a humidified CPAP system.

Figure 3:
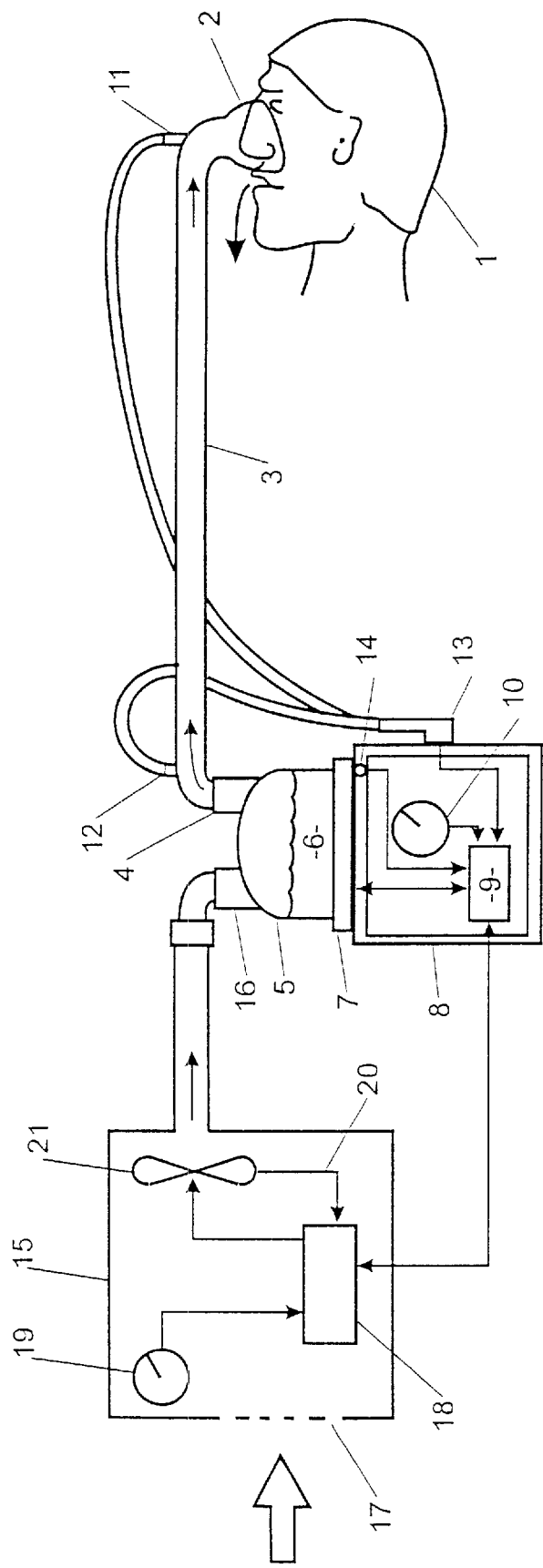
FIG. 3 is a block diagram of a humidified continuous positive airway pressure (CPAP system) as might be used in conjunction with the present invention.

With reference to FIG. 3 a humidified Continuous Positive Airway Pressure (CPAP) system is shown in which a patient 1 is receiving humidified and pressurised gases through a nasal mask 2 connected to a humidified gases transportation pathway or inspiratory conduit 3. It should be understood that delivery systems could also be VPAP (Variable Positive Airway Pressure) and BiPAP (Bi-level Positive Airway Pressure) or numerous other forms of respiratory therapy. Inspiratory conduit 3 is connected to the outlet 4 of a humidification chamber 5 which contains a volume of water 6. Inspiratory conduit 3 may contain heating means or heater wires (not shown) which heat the walls of the conduit to reduce condensation of humidified gases within the conduit. Humidification chamber 6 is preferably formed from a plastics material and may have a highly heat conductive base (for example an aluminium base) which is in direct contact with a heater plate 7 of humidifier 8. Humidifier 8 is provided with control means or electronic controller 9 which may comprise a microprocessor based controller executing computer software commands stored in associated memory.

Controller 9 receives input from sources such as user input means or dial 10 through which a user of the device may, for example, set a predetermined required value (preset value) of humidity or temperature of the gases supplied to patient 1. The controller may also receive input from other sources, for example temperature and/or flow velocity sensors 11 and 12 through connector 13 and heater plate temperature sensor 14. In response to the user set humidity or temperature value input via dial 10 and the other inputs, controller 9 determines when (or to what level) to energise heater plate 7 to heat the water 6 within humidification chamber 5. As the volume of water 6 within humidification chamber 5 is heated, water vapour begins to fill the volume of the chamber above the water's surface and is passed out of the humidification chamber 5 outlet 4 with the flow of gases (for example air) provided from a gases supply means or blower 15 which enters the chamber through inlet 16. Exhaled gases from the patient's mouth are passed directly to ambient surroundings in FIG. 3.

Blower 15 is provided with variable pressure regulating means or variable speed fan 21 which draws air or other gases through blower inlet 17. The speed of variable speed fan 21 is controlled by electronic controller 18 (or alternatively the function of controller 18 could carried out by controller 9) in response to inputs from controller 9 and a user set predetermined required value (preset value) of pressure or fan speed via dial 19.

Nasal Mask

Figure 4:
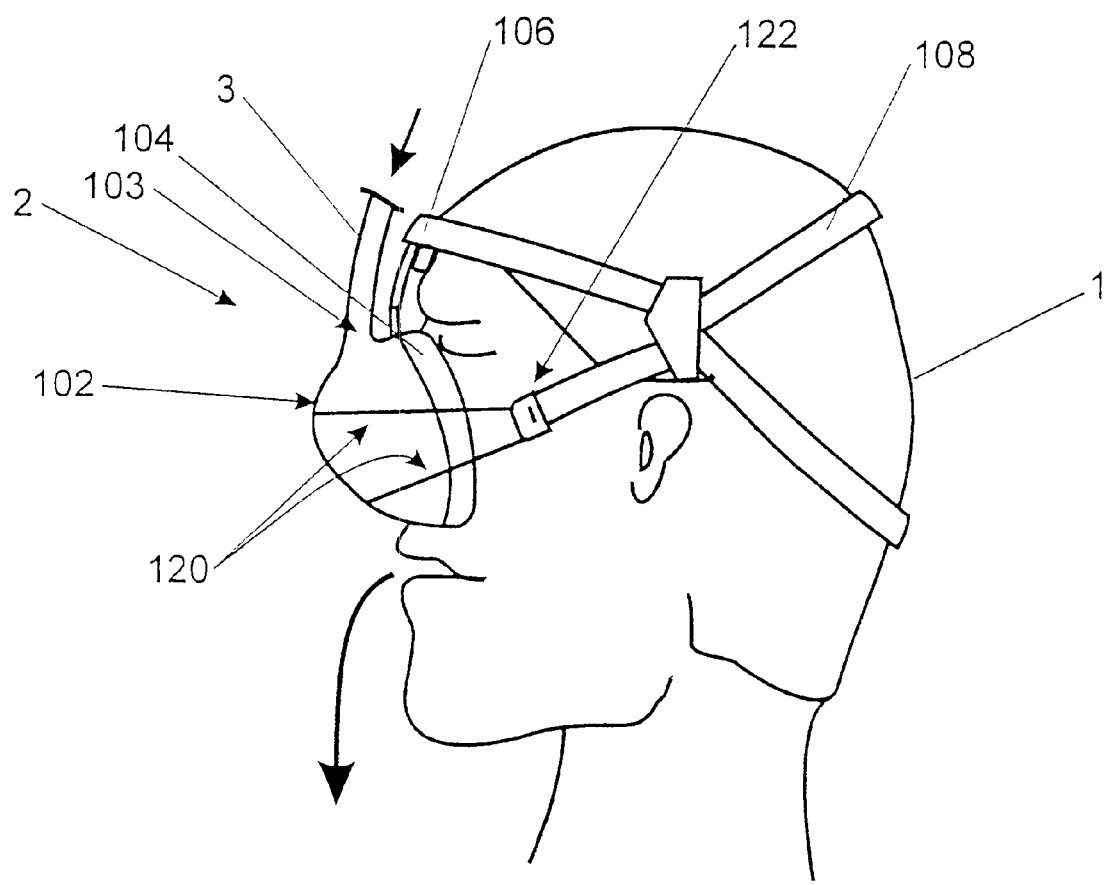
FIG. 4 is an illustration of the nasal mask in use according to the preferred embodiment of the present invention.

Referring to FIG. 4 the nasal mask, according to the preferred embodiment of the present invention, is shown in detail. The mask includes a hollow body 102 with an inlet 103 connected to the inspiratory conduit 3. The mask 2 is positioned around the nose of the user 1 with the headgear 108 secured around the back of the head of the patient 1. The restraining force from the headgear 108 on the hollow body 102 and the forehead rest 106 ensures enough compressive force on the mask cushion 104, to provide an effective seal against the patient's face.

The hollow body 102 is constructed of a relatively inflexible material for example, polycarbonate plastic. Such a material would provide the requisite rigidity as well as being transparent and a relatively good insulator. The expiratory gases can be expelled through a valve (not shown) in the mask, a further expiratory conduit (not shown), or any other such method as is known in the art.

Mask Headgear

Figure 5:
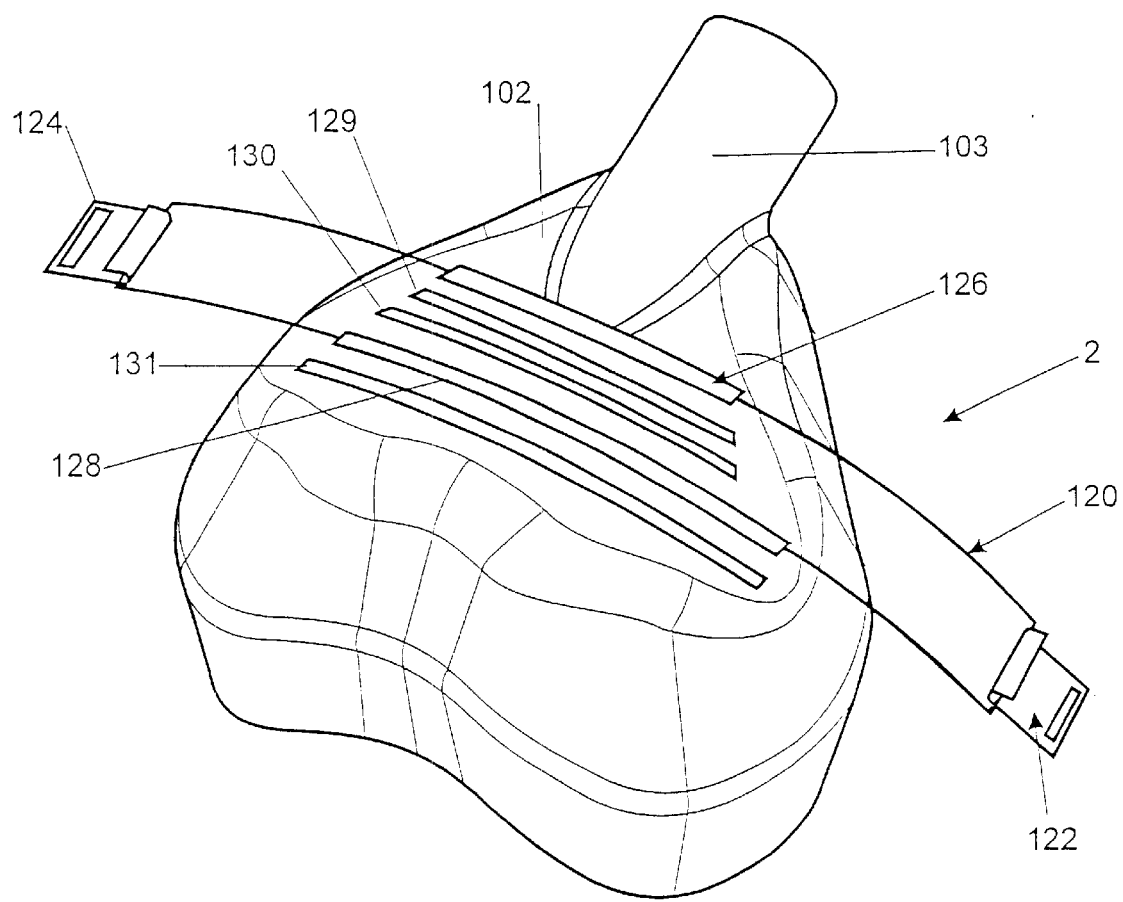
FIG. 5 is a front view of the nasal mask illustrating the headgear securement to the mask.

Referring now to FIGS. 4 and 5 the headgear 108 is shown connected to the hollow body 102. Rather than traditional fixed or adjustable attachments the present invention utilises a sliding engagement between the headgear 108 and the hollow body 102. This is achieved with a loop 120, running through harnessing clips 122, 124 on either side of the headgear 108 and over the top of the hollow body 102. The loop 120 is reciprocally engaged with guides 126, 128 mounted on the top surface of the hollow body 102. The guides constrain the loop 120 but allow it to slide in and out, meaning the headgear 108 can move laterally, independently of the hollow body 102.

The advantage to this is as the face is contorted during various sleeping positions the headgear is able to move with the changes in position while the mask is left in the correct position on the nose of the user and an effective seal is maintained.

Additional guides 129, 130, 131 allow the user to adjust position of loop 120, giving ability to get different pressure on the seal depending on loop 120 position.

To further ensure user comfort and effective pressure on the mask cushion 104, the headgear 108 may be constructed either using two straps running around the back of the user's head as shown in FIG. 4 or with a partial skull cap or any other configurations as are known in the art. In this case the straps or partial skull cap would be constructed using neoprene but may also be constructed using any material as is known in the art which will be comfortable for the user.

Figure 6:
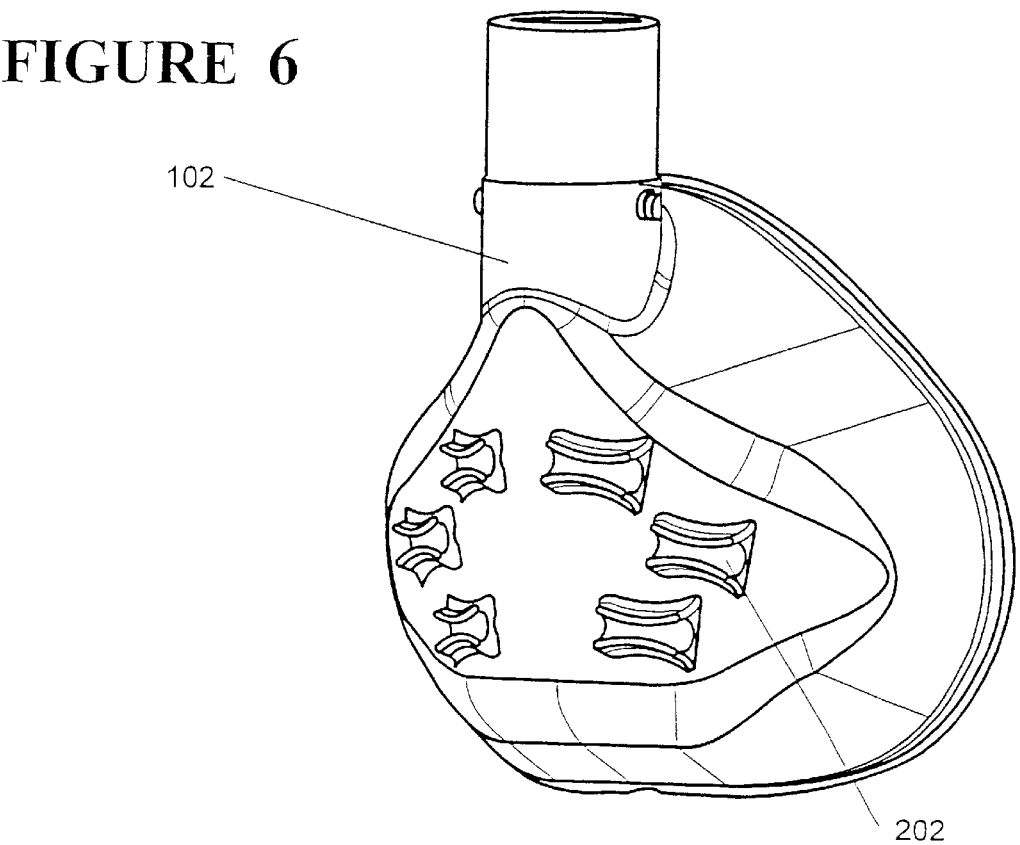
FIG. 6 is a perspective view of the mask showing multiple engaging clips.
Figure 7:
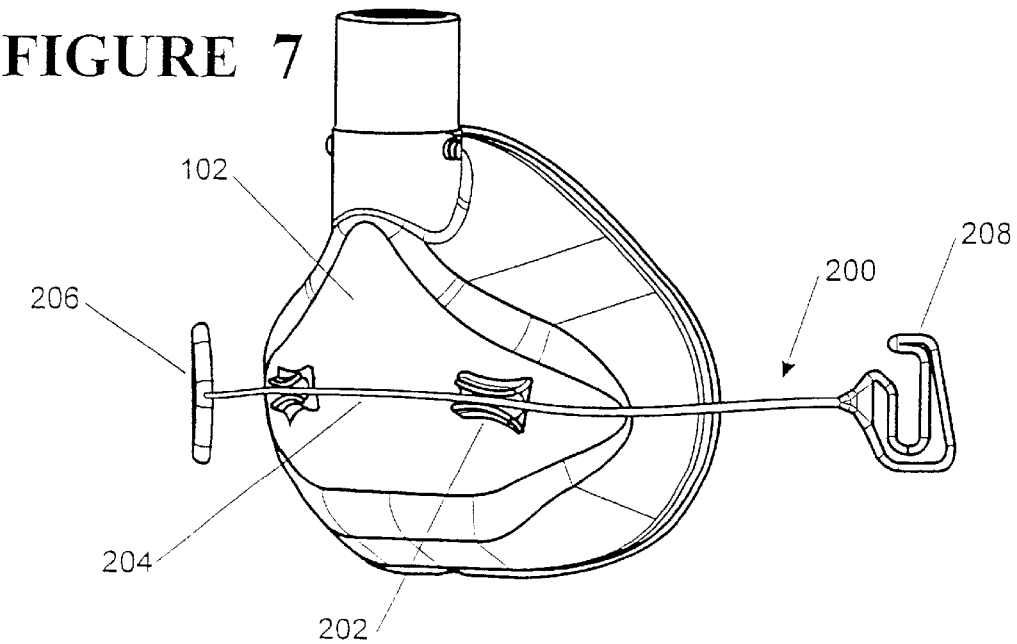
FIG. 7 is a perspective view of the mask showing the sliding strap clipped in place.
Figure 8:
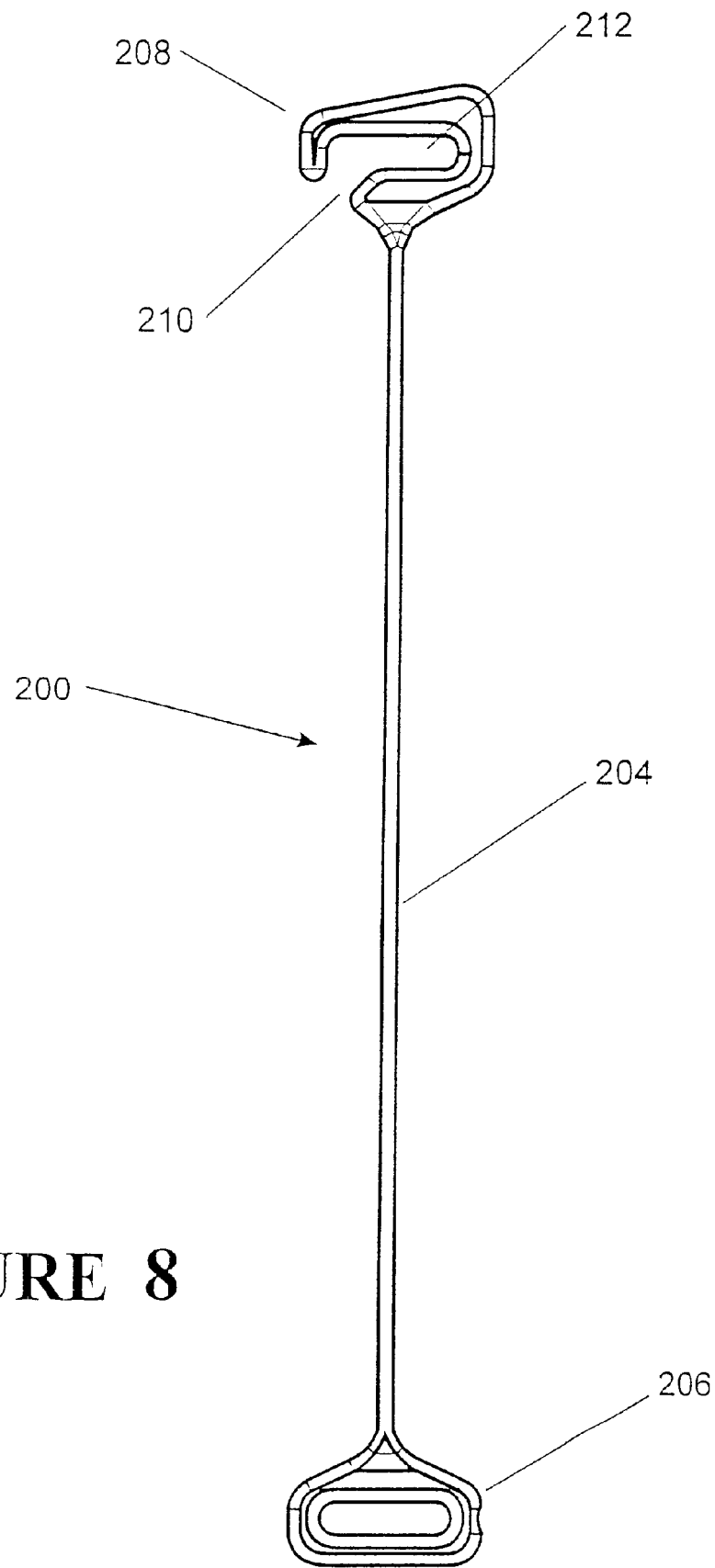
FIG. 8 is a side view of the sliding strap.

In a further embodiment shown in FIGS. 6, 7 and 8 the present invention is illustrated using a sliding strap to attach the headgear 108 to the hollow body 102. The strap 200, shown in FIG. 8 in isolation, is constructed of polyacetal (Delrin 500P NC010) using injection moulding techniques to give a polished finish. This material, similar to other nylon based derivatives, with its polished finish has a particularly low friction co-efficient, and therefore slides with respect to the hollow body 102 with very little resistance.

As shown in FIG. 6, the hollow body 102 includes a number of engaging clips 202, in use the sliding strap 200 snaps into place into the engaging clips 202 and can only be removed therefrom using a substantial force. This means that with any normal use the sliding strap 200 will stay retained within the engaging clips 202. It will also be appreciated from FIG. 6 that a number of clips are so provided, in order to allow pressure from different angles for different face shapes.

As shown in FIG. 8 the sliding strap includes a midsection 204 intended to reciprocate with the engaging clips 202, terminated at each end by loops 206, 208 which attach to the headgear. The first loop 206 is a full loop through which the headgear 108 is permanently attached with for example, a velcro strap. The loop 208 at the other end, is only a partial loop 210 designed so that a strap or loop from the headgear 108 can be easily slipped in or out of the open section 212 to allow easy removal and attachment of the mask.

Figure 1:
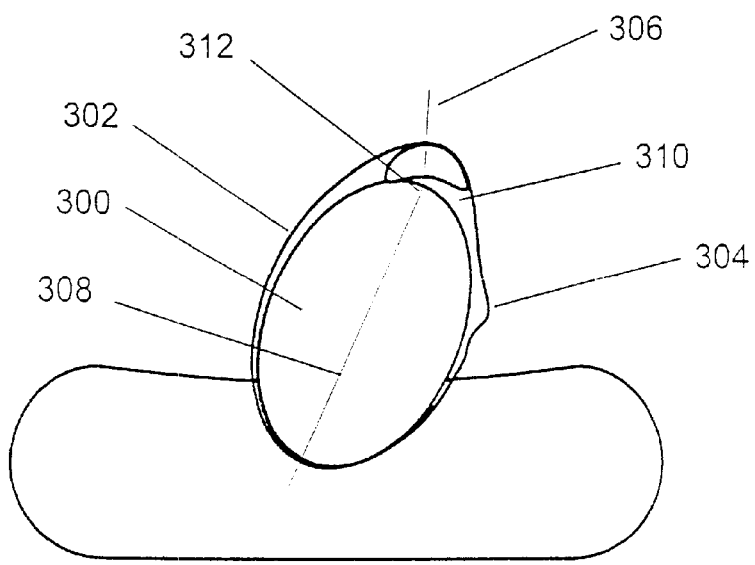
FIG. 1 is a plan view of a prior art mask illustrating side leak.
Figure 2:
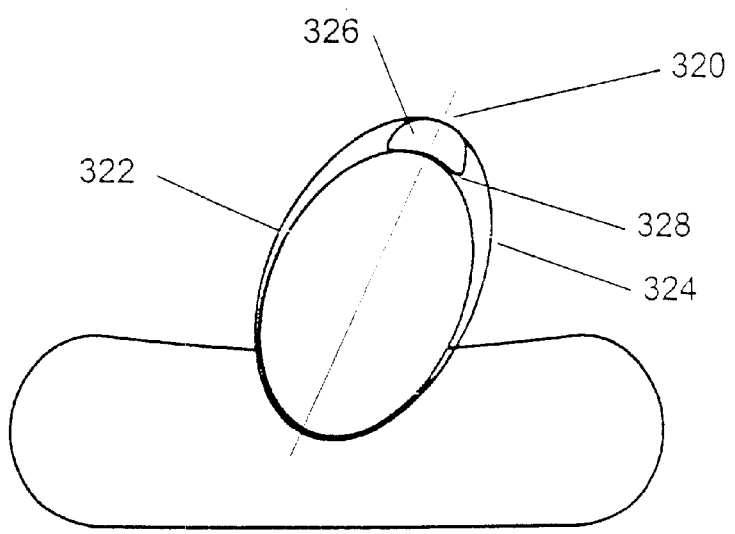
FIG. 2 is a plan view of a mask according to the preferred embodiment of the present invention.

It will be appreciated that in all embodiments of the present invention the attachment from the headgear to the mask is designed to slide with as less friction as possible while still ensuring adequate direct force on the mask cushion to the user's face. As shown in FIG. 2 the sliding connection 320 allows the headgear 322,324 to provide even force on both sides of the mask 326. This avoids placing a torque on the mask and twisting of the mask which minimises mask leaks from the seal to the face 328.

What is claimed is:

1. A device for delivering a supply of gases to a user comprising:

a patient interface, adapted to be in fluid communication with said supply of gases, and adapted to provide a substantially sealed flow path for said flow of gases to said user in at least a correct orientation and position on said user, headgear adapted to attach to or around the head of said user, and a sliding connection between said headgear and said patient interface when said patient interface is engaged with a face of the user.

2. A device as claimed in claim 1 wherein said patient interface is a nasal mask.

3. A device as claimed in claim 2 wherein said nasal mask comprises a body portion having an inlet receiving said supply of gases, and sealing means attached to or integrated with said body portion, said sealing means adapted to seal against the facial contours of said user.

4. A device as claimed in claim 3 wherein said sliding connection is adapted to allow said headgear substantial movement with respect to said nasal mask, while still providing compressive force on said sealing means to ensure said supply of gases is delivered to said user without significant leakage.

5. A device as claimed in any one of claims 1 to 4 wherein said headgear comprises a member engaged thereto, said engagement between said headgear and said member adapted to allow temporary release therefrom.

6. A device as claimed in claim 5 wherein said member is elongate having a first end and second end, a first at least partial loop located at said first end and a second at least partial loop located at said second end, whereby in use said headgear is substantially permanently attached to said first loop and substantially attached but readily releasable from said second loop.

7. A device as claimed in claim 5 wherein said patient interface further comprises at least one restraining means on said body portion, in use said member is restrained in at least one axis by, but which can slide easily within at least one other dimension, said restraining means and can be easily disengaged therewith.

8. A device as claimed in claim 6 wherein said patient interface further comprises at least one restraining means on said body portion, in use said member is restrained in at least one axis by, but which can slide easily within at least one other dimension, said restraining means and can be easily disengaged therewith.

9. A device as claimed in claim 1 wherein said headgear includes a low resistance sliding strap slidingly connected on, through, adjacent or with said patient interface.

10. A device as claimed in claim 9 wherein said sliding strap is molded from polyacetal.

11. A device as claimed in claim 1 wherein said headgear includes a low resistance sliding loop slidingly connected on, through, adjacent or with said patient interface.

12. A device as claimed in claim 11 wherein said sliding loop comprises a looped nylon filament.

13. A nasal mask for delivering gases to a user comprising:

a body portion having an inlet, in use said inlet receiving a supply of gases, sealing means engaged with said body portion, and adapted to seal against the facial contours of said user, and engaging means adapted to in use provide a sliding engagement with a means of securement to a user when said nasal mask is engaged with a face of the user, and a compressive force on said sealing means to ensure said supply of gases is delivered to a user without significant leakage.

14. A nasal mask as claimed in claim 13 wherein said engaging means comprises a restraining means, said restraining means adapted to in use accommodate an elongate member, said restraining means adapted to in use restrain said member in at least one dimension, but allow said member to slide easily within at least one other dimension, and providing a compressive force on said sealing means to avoid any significant leakage, said restraining means adapted to in use easily disengage with said member.

15. In a CPAP system for delivering gases to a user comprising a pressurized source of gases, a conduit in fluid communication with said pressurized source adapted to convey said gases, a patient interface in fluid communication with said conduit in use delivering said gases to said user, and headgear attaching said interface with said user, the improvement comprising that said patient interface adapted to sliding engage with said headgear when said patient interface is engaged with a face of the user, to ensure said supply of gases is delivered to a user without significant leakage.

16. In a CPAP system as claimed in claim 15 the improvement further comprising that said system further comprises a humidifier to variably humidify said gases.

17. A device for delivering a supply of gases to a user comprising:

a patient interface, adapted to be in fluid communication with said supply of gases, and adapted to provide a substantially sealed flow path for said flow of gases to said user in at least a correct orientation and position on said user, and headgear including at least a partial loop adapted to engage said patient interface and pass across the face of said user.

18. A device as claimed in claim 17 wherein said loop is adapted to pass over and slidingly engage with said interface.

19. A device as claimed in claim 17 wherein said loop is adapted to pass at least partially through and slidingly engage with said interface.

* * * * *

UNITED STATES PATENT AND TRADEMARK OFFICE
CERTIFICATE OF CORRECTION

PATENT NO. : 6,615,834 B2  Page 1 of 1
DATED : September 9, 2003
INVENTOR(S) : Lewis George Gradon et al.

It is certified that error appears in the above-identified patent and that said Letters Patent is hereby corrected as shown below:

<u>Title page,</u>
Item [56], References Cited, U.S. PATENT DOCUMENTS, add the following references:

| -- 2,414,405 | 01/14/47 | Bierman et al. |
| 2,837,090 | 06/03/58 | Bloom et al. |
| 5,662,101 | 09/02/97 | Ogden et al. |
| 5,832,918 | 11/10/98 | Pantino |
| 5,975,079 | 11/02/99 | Hellings et al. -- |

Signed and Sealed this

Twentieth Day of January, 2004

JON W. DUDAS
*Acting Director of the United States Patent and Trademark Office*